United States Patent
Hijiya et al.

(10) Patent No.: US 6,761,767 B2
(45) Date of Patent: Jul. 13, 2004

(54) PRODUCTION METHOD OF FAMCICLOVIR AND PRODUCTION AND CRYSTALLIZATION METHOD OF INTERMEDIATE THEREFOR

(75) Inventors: Toyoto Hijiya, Yokkaichi (JP); Takayoshi Torii, Kawasaki (JP); Kunisuke Izawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 8 days.

(21) Appl. No.: 10/231,249

(22) Filed: Aug. 30, 2002

(65) Prior Publication Data

US 2003/0056712 A1 Mar. 27, 2003

(30) Foreign Application Priority Data

Aug. 30, 2001 (JP) .................................. 2001-262301

(51) Int. Cl.$^7$ .......................... C30B 25/00; C30B 25/04
(52) U.S. Cl. ........................................ 117/68; 117/70
(58) Field of Search ........................................ 117/68

(56) References Cited

FOREIGN PATENT DOCUMENTS

| EP | 0 728 757 | 8/1996 |
|----|-----------|--------|
| EP | 0 827 960 | 3/1998 |
| EP | 0 916 674 | 5/1999 |
| JP | 11-180983 | 7/1999 |
| WO | WO 99/51603 | 10/1999 |
| WO | WO 99/51604 | 10/1999 |
| WO | WO 00/06573 | 2/2000 |

OTHER PUBLICATIONS

D.-K Kim, et al., Bioorganic & Medicinal Chemistry, vol. 7, pp. 565–570, XP–002220538, "Synthesis and Evaluation of 2–Amino–6–Fluoro–9–(4–Hydroxy–3–Hydroxymethylbut–1–yl)Purine Mono–and Diesters as Potential Prodrugs of Penciclovir", 1999.

M. R. Harnden , et al., Journal of Medicinal Chemistry, vol. 30, pp. 1636–1642, XP–002220539, "Synthesis and Antiviral Activity of 9–[4–Hydroxy–3–(Hydroxymethyl)But–1–yl]Purines", 1987.

G. R. Geen, et al., Tetrahedron, vol. 46, No. 19, pp. 6903–6914, "The Effect of the C–6 Substituent on the Regioselectivity of N–Alkylation of 2–Aminopurines", 1990.

B. M. Choudary, et al. Nucleosides & Nucleotides, vol. 15, No. 5, pp. 981–994, "A Direct Approach to the Synthesis of Famciclovir and Penciclovir", 1996.

G. R. Geen, et al., Tetrahedron Letters, vol. 42, pp. 1781–1784, Regioselective Alkylation of Guanines using 2–Acetoxytetrahydrofurans, 2001.

R. Freer, et al., Tetrahedron, vol. 56, pp. 4589–4595, "A New Route to Famciclovir via Palladium Catalysed Allylation", 2000.

*Primary Examiner*—Felisa Hiteshew
(74) *Attorney, Agent, or Firm*—Oblon, Spivak, McClelland, Maier & Neustadt, P.C.

(57) ABSTRACT

An N-9-position alkylated form is selectively precipitated by subjecting a mixture containing the N-9-position alkylated form and an N-7-position alkylated form of 2-amino-6-halopurine to a crystallization step using a mixed solvent of an organic solvent and water. Then, this N-9-position alkylated form is reduced to give famciclovir. By this method of the present invention, famciclovir known as an antiviral agent, and an intermediate compound therefor can be efficiently produced.

33 Claims, No Drawings

PRODUCTION METHOD OF FAMCICLOVIR AND PRODUCTION AND CRYSTALLIZATION METHOD OF INTERMEDIATE THEREFOR

TECHNICAL FIELD OF THE INVENTION

The present invention relates to industrial production and crystallization methods of famciclovir known as an antiviral agent and an intermediate compound therefor.

BACKGROUND OF THE INVENTION

A 2-amino-6-halopurine derivative of the formula (3)

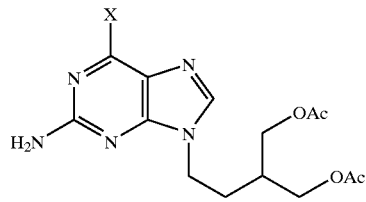

(3)

wherein X is a chlorine atom, a bromine atom or an iodine atom and Ac is an acetyl group, is known as an important intermediate compound for famciclovir of the formula (4)

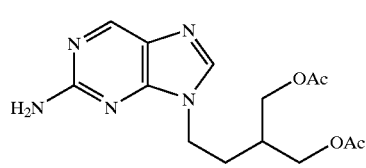

(4)

known as an antiviral agent.

The 2-amino-6-halopurine derivative (hereinafter to be also referred to as an N-9-position alkylated form) of the formula (3) can be obtained by reacting 2-amino-6-halopurine of the formula (1) with a compound of the formula (2) as shown in the following formulas:

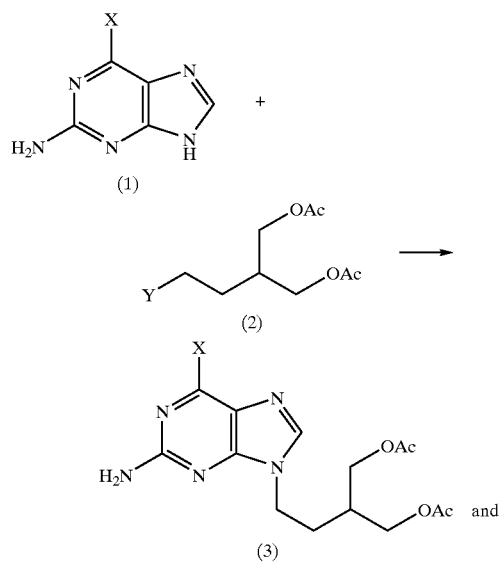

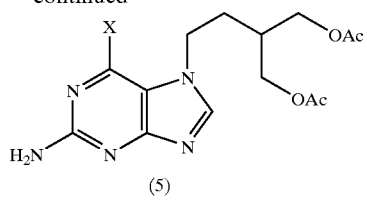

(5)

Depending on the reaction, however, a 2-amino-6-halopurine derivative of the formula (5) (hereinafter to be also referred to as an N-7-position alkylated form) is by-produced as an impurity. This impurity is difficult to separate, and the separation has conventionally required silica gel chromatography, as taught in Tetrahedron, 46, page 6903 (1990).

In addition, a produce method of famciclovir through a different compound, which is free of silica gel chromatography, has been known. For example, Nucleosides & Nucleotides, 15, page 981 (1996), Tetrahedron, 56, page 4589 (2000), Tetrahedron letters, 42, page 1781 (2001), EP0728757A, EP0827960A and the like can be mentioned. However, since these methods require a number of steps, a more efficient production method has been demanded.

Accordingly, the present invention aims at providing an efficient production method of famciclovir known as an antiviral agent and an intermediate compound therefor.

SUMMARY OF THE INVENTION

As a result of the intensive investigation of the present inventors, it has been found according to the present invention that, by subjecting a mixture containing an N-7-position alkylated form and an N-9-position alkylated form to a crystallization step using a mixed solvent of an organic solvent and water, the objective N-9-position alkylated form precipitates selectively and the N-7-position alkylated form can be removed highly.

Accordingly, the present invention provides the following.

[1] A production method of a 2-amino-6-halopurine derivative represented by the formula (3), which comprises subjecting a mixture containing 2-amino-6-halopurine derivatives represented by the formulas:

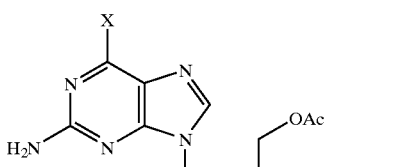

(3)

and

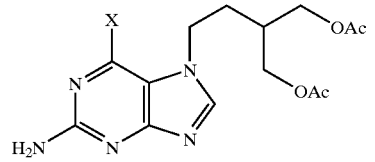

(5)

wherein X is a chlorine atom, a bromine atom or an iodine atom and Ac is an acetyl group, to a crystallizing step using a mixed solvent of an organic solvent and water to selectively precipitate the 2-amino-6-halopurine derivative represented by the formula (3).

[2] The production method of the above-mentioned [1], wherein the mixture containing the 2-amino-6-halopurine derivatives represented by the formulas (3) and (5) is obtained by reacting 2-amino-6-halopurine represented by the formula (1):

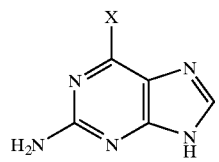
(1)

wherein X is as defined in the above-mentioned [1], with a compound represented by the formula (2):

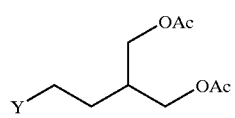
(2)

wherein Y is a leaving group and Ac is as defined in the above-mentioned [1].

[3] The production method of the above-mentioned [1] or [2], wherein X is a chlorine atom.

[4] The production method of the above-mentioned [2], wherein the leaving group represented by Y is a group selected from the group consisting of a chlorine atom, a bromine atom, an iodine atom, a p-toluenesulfonyloxy group, a mesyloxy group, a trifluoromethanesulfonyloxy group, an alkylcarbonate group, a phenylcarbonate group and a saturated or unsaturated acyloxy group.

[5] The production method of the above-mentioned [2], wherein the 2-amino-6-halopurine represented by the formula (1) is reacted with the compound represented by the formula (2) in the same organic solvent as used for crystallization.

[6] The production method of any of the above-mentioned [1] to [5], wherein the organic solvent is at least one selected from the group consisting of dimethylformamide, N-methylpyrrolidone, 1,3-dimethyl-2-imidazolidinone and dimethylacetamide.

[7] The production method of the above-mentioned [2], wherein the 2-amino-6-halopurine represented by the formula (1) is reacted with the compound represented by the formula (2) in the presence of a base.

[8] The production method of the above-mentioned [7], further comprising neutralization of a reaction mixture by using an acid after completion of the reaction.

[9] The production method of any of the above-mentioned [1] to [8], wherein the crystallization is cooling crystallization.

[10] A production method of famciclovir represented by the formula (4):

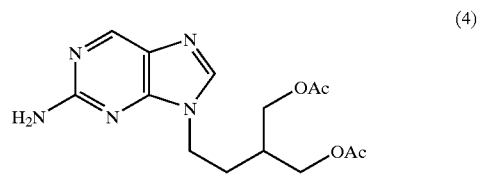
(4)

wherein Ac is an acetyl group, which comprises obtaining the 2-amino-6-halopurine derivative represented by the formula (3) according to any of the above-mentioned [1] to [9], and then reducing the 2-amino-6-halopurine derivative.

[11] A method of selectively crystallizing a 2-amino-6-halopurine derivative represented by the formula (3), which comprises subjecting a mixture containing 2-amino-6-halopurine derivatives represented by the formulas:

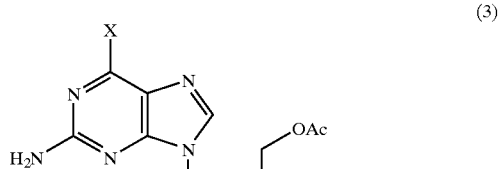
(3)
and

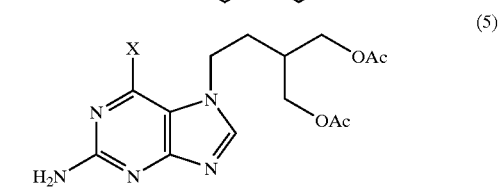
(5)

wherein X is a chlorine atom, a bromine atom or an iodine atom and Ac is an acetyl group, to a crystallization step using a mixed solvent of an organic solvent and water.

[12] The crystallization method of the above-mentioned [11], wherein X is a chlorine atom.

[13] The crystallization method of the above-mentioned [11], wherein the organic solvent is at least a member selected from the group consisting of dimethylformamide, N-methylpyrrolidone, 1,3-dimethyl-2-imidazolidinone and dimethylacetamide.

[14] The crystallization method of the above-mentioned [11], wherein the crystallization is cooling crystallization.

DETAILED DESCRIPTION OF THE INVENTION

The present invention is explained in detail in the following.

In the formula (1), the formula (3) and the formula (5) in the present invention, X represents a chlorine atom, a bromine atom or an iodine atom, with most preference given to a chlorine atom.

In the formula (2) of the present invention, Y represents a leaving group. The leaving group is not particularly limited and is, for example, a halogen atom (e.g., chlorine atom, bromine atom, iodine atom), a sulfonyloxy group (e.g., p-toluenesulfonyloxy group, mesyloxy group, trifluoromethanesulfonyloxy group and the like), an acyloxy group (preferably saturated or unsaturated acyloxy group having 1 to 8 carbon atoms in total, such as a group represented by R—C(=O)—O— wherein R is an aryl group optionally substituted by alkyl group (preferably having 6 to 8 carbon atoms in total, such as phenyl group, p-tolyl group and the like), an aryloxy group optionally substituted by alkyl group (preferably having 6 to 8 carbon atoms in total such as phenoxy group, p-tolyloxy group and the like), aralkyl group (preferably having 7 to 9 carbon atoms in total such as benzyl group and the like), arylalkenyl group (preferably having 8 or 9 carbon atoms in total such as cinnamyl group and the like), aralkyloxy group (having 7 to 15 carbon atoms in total such as benzyloxy group, 9-fluorenylmethyloxy group and the like), or alkoxy group (linear or branched chain alkoxy group having 1 to 8 carbon atoms such as methoxy, ethoxy, t-butoxy and the like), and the like. Of these, chlorine atom, bromine atom, iodine atom, p-toluenesulfonyloxy group, mesyloxy group, trifluoromethanesulfonyloxy group, alkylcarbonate group, phenylcarbonate group and saturated or unsaturated acyloxy group and the like are preferable, particularly preferably bromine atom and mesyloxy group.

First, a step for crystallizing a mixture containing an N-7-position alkylated form and an N-9-position alkylated form (hereinafter to be also simply referred to as a mixture) is explained.

In the crystallization step of the present invention, the crystallization solvent is not only an organic solvent but water, which is a poor solvent to a mixture containing an N-7-position alkylated form and an N-9-position alkylated form. Using this mixed solvent, a mixture containing the N-7-position alkylated form and the N-9-position alkylated form is subjected to crystallization to selectively precipitate the N-9-position alkylated form.

The crystallization in the present invention means a conventional operation such as (1) a step for precipitating crystals from a solution, in which a crystalline substance (N-9-position alkylated form) is dissolved, comprising concentration by evaporating the solvent, (2) a step for precipitating a crystal from a solution, in which a crystalline substance (N-9-position alkylated form) is dissolved, comprising lowering the temperature, thereby to make the concentration higher than the saturated solubility (also to be referred to as cooling crystallization), (3) a step for precipitating a crystal by adding a suitable amount of water, which is a poor solvent, to a solution, in which a crystalline substance (N-9-position alkylated form) is dissolved, to make the concentration higher than the saturated solubility, and the like. In the present invention, the cooling crystallization is preferable for improving the purity of the N-9-position alkylated form. The crystallization is preferably carried out under stirring.

The solvent to be used for the crystallization step is a mixed solvent of an organic solvent and water, wherein the amount of water to be used is preferably 0.5 to 1.5-fold, more preferably 0.7 to 1.1-fold, in a volume ratio to the organic solvent.

Examples of the organic solvent in the mixed solvent used for the crystallization step include an amide solvent (e.g., dimethylformamide (DMF), N-methylpyrrolidone, 1,3-dimethyl-2-imidazolidinone, dimethylacetamide etc.), dimethyl sulfoxide (DMSO), acetonitrile and the like, which is preferably an amide solvent, more preferably DMF, N-methylpyrrolidone, 1,3-dimethyl-2-imidazolidinone and dimethyl acetamide. Of these, DMF is particularly preferable. These organic solvents may be used alone or in combination of two or more kinds thereof.

The amount of use of the mixed solvent may be varied as appropriate depending on the mixing ratio, crystallization conditions and the like. For example, when a mixed solvent of water and DMF (water:DMF (volume ratio)=1:1–396:7) is used for crystallization under the above-mentioned crystallization conditions, 6–15 ml of a mixed solvent is preferably used per 1 mmol of a mixture containing an N-7-position alkylated form and an N-9-position alkylated form.

In the following, the crystallization in the present invention is explained by referring to a preferable embodiment (cooling crystallization) as an example. The present invention is not limited to the example.

By dissolving a mixture containing an N-7-position alkylated form and an N-9-position alkylated form with heating in a mixed solvent of water and an organic solvent and then cooling, an N-9-position alkylated form is selectively precipitated. The order of addition of the compound and the solvent is not particularly limited. For example, after dissolving a mixture containing an N-7-position alkylated form and an N-9-position alkylated form in an organic solvent, water is added; a mixture containing an N-7-position alkylated form and an N-9-position alkylated form is added to a mixed solvent of an organic solvent and water prepared in advance and the like.

The temperature during dissolving with heating is not particularly limited as long as it is a temperature at which the mixture can be dissolved in the mixed solvent, and varies depending on the mixed solvent to be used. Generally, heating at not lower than 50° C., preferably 50–80° C., more preferably 50–60° C., results in complete dissolution of the mixture.

After dissolution of the mixture with heating, the solution is cooled to allow precipitation of the desired N-9-position alkylated form. The cooling temperature is not particularly limited as long as it is a temperature at which a desired compound precipitates, which is preferably 0–30° C., more preferably 10–20° C. The cooling can be preferably done at a cooling rate of 1–10° C./hr, more preferably at 2–5° C./hr.

The crystal precipitated by cooling is preferably aged for a given time. The aging can be done at the cooling temperature preferably for 1–24 hr, more preferably 2–12 hr.

The crystallization method other than the cooling crystallization, such as the methods of the above-mentioned (1) and (3) can be performed under the conditions appropriately determined based on the explanation of the above-mentioned cooling crystallization. For example, in the method (1), the organic solvent may be evaporated from the solution so that the conditions, such as the mixing ratio of an organic solvent and water, the amount of use of the mixed solvent relative to the N-9-position alkylated form and the like, may fall within the above-mentioned range. In the method (3), water is added to the solution of an organic solvent while adjusting to meet the above-mentioned mixing ratio of the organic solvent and water, and the temperature is appropriately adjusted to crystallize the N-9-position alkylated form.

The obtained crystal can be separated by a conventional method such as filtration and the like. To increase the purity of the crystal, the crystal may be washed with, for example, a mixed solvent of DMF and water, water and the like. Alternatively, the obtained crystal is subjected again to a similar crystallization step to further increase the purity of the crystal.

In this way, a crystal of an N-9-position alkylated form highly free of an impurity, an N-7-position alkylated form, can be obtained. That is, the method of the present invention comprising subjecting a mixture containing an N-9-position alkylated form and an N-7-position alkylated form to a crystallization step using a mixed solvent of an organic solvent and water, selectively affords a crystal of an N-9-position alkylated form.

The crystallization step in the present invention is particularly useful for a mixture containing an N-7-position alkylated form and an N-9-position alkylated form, which results from a reaction simultaneously producing the N-7-position alkylated form and the N-9-position alkylated form. This is because the N-7-position alkylated form and the N-9-position alkylated form are difficult to separate, but the N-9-position alkylated form can be separated easily by applying the mixture to the crystallization step of the present invention. In the following, as the production method of a mixture to be subjected to the crystallization step, a method simultaneously affording an N-7-position alkylated form and an N-9-position alkylated form is explained as an example, but the production method of the mixture of the present invention is not limited to this method.

A mixture containing an N-7-position alkylated form and an N-9-position alkylated form to be subjected to the crystallization step can be produced by a known method. For example, the mixture is obtained by the method described in Tetrahedron, 46, page 6903 (1990), namely, by reacting 2-amino-6-halopurine represented by the formula (1) with a compound represented by the formula (2). This reaction is generally carried out in a reaction solvent.

The amount of use of a compound represented by the formula (2) is generally 0.5 to 2-fold mol, preferably 1 to 1.5-fold mol, relative to 2-amino-6-halopurine represented by the formula (1).

As the reaction solvent, for example, an amide solvent (e.g., DMF, N-methylpyrrolidone, 1,3-dimethyl-2-imidazolidinone, dimethylacetamide etc.), acetonitrile, DMSO and the like can be mentioned, preferably an amide solvent, more preferably DMF, N-methylpyrrolidone, 1,3-dimethyl-2-imidazolidinone, dimethylacetamide and the like. Particularly, DMF is preferable. These organic solvents may be used alone or in combination of two or more thereof.

The amount of use of the reaction solvent is such an amount as to make the concentration of 2-amino-6-halopurine represented by the formula (1) in a reaction solvent preferably 0.05–1 mol/L, more preferably 0.2–0.5 mol/L.

The mixture is generally produced in the presence of a base. Examples of the preferable base include an inorganic base such as potassium carbonate, sodium carbonate, cesium carbonate and the like, a quaternary ammonium salt such as tetrabutylammonium hydroxide and the like, and the like. The amount of the base to be used is preferably 0.5 to 2-fold mol, more preferably 1 to 1.5-fold mol of 2-amino-6-halopurine represented by the formula (1).

The reaction temperature is generally 0–80° C., preferably 20–50° C. The reaction time is generally 2–48 hr, preferably 5–25 hr. If necessary, the reaction may be further conducted at 50–100° C. for 1–5 hr to complete the reaction.

After completion of the reaction, reaction solvent may be removed from the reaction solution by concentration and the like as necessary. When the reaction solvent can be used for the crystallization step, the above-mentioned crystallization may be generally applied without concentration and the like. Thus, the use of the same organic solvent for the reaction and the crystallization step is preferable because it is economical and industrially beneficial since the number of steps can be reduced.

When the reaction is conducted in the presence of a base, the reaction mixture may be neutralized with an acid and subjected to the next crystallization step. The acid to be used for neutralization is, for example, an organic acid such as acetic acid, citric acid and the like and an inorganic acid such as hydrochloric acid, sulfuric acid and the like, with preference given to organic acid. For neutralization, the reaction solution need only to be adjusted to generally pH 5–9, preferably pH 6–8.

When a mixture containing an N-7-position alkylated form and an N-9-position alkylated form, which was obtained by the above-mentioned method, is subjected to a crystallization step using a solvent usable for the crystallization step as a reaction solvent, for example, water is added in excess to the reaction solution to allow precipitation of the crystal of N-9-position alkylated form. Preferably, a suitable amount of water is added to the reaction solution to give a mixed solvent, which is heated to a suitable temperature and subjected to cooling crystallization. The suitable amount of water and suitable temperature for heating are the same as those for the above-mentioned crystallization step. When water is added to a reaction solution to give a mixed solvent, a crystal is generally precipitated but when cooling crystallization is carried out, a precipitated crystal is preferably dissolved once by heating to a suitable temperature.

The obtained 2-amino-6-halopurine derivative (N-9-position alkylated form) is reduced to give famciclovir known as an antiviral agent. As described in Nucleosides & Nucleotides, 15, page 981 (1996), for example, a 2-amino-6-halopurine derivative (N-9-position alkylated form) is subjected to catalytic reduction using palladium carbon as a catalyst in a solvent such as ethyl acetate and the like in the presence of a base such as triethylamine and the like to give famciclovir.

While the present invention is explained in detail in the following by referring to Examples, the present invention is not limited by these examples in any way.

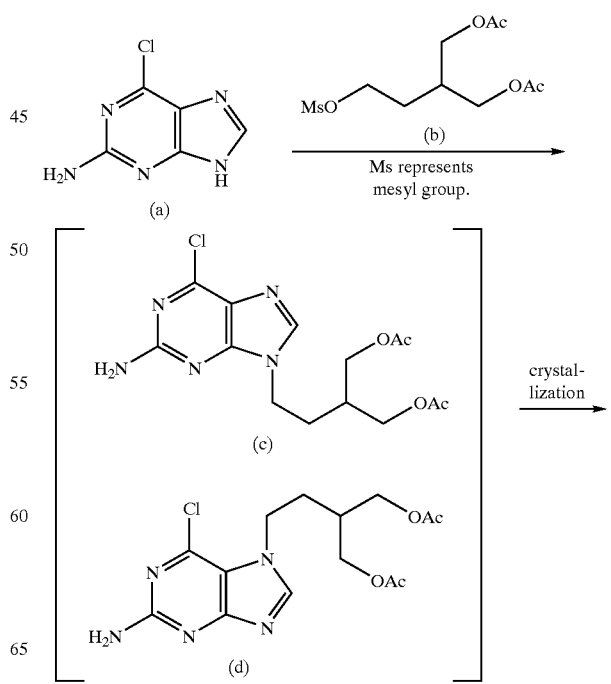

-continued

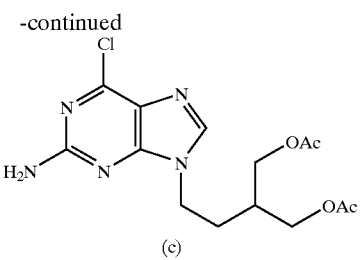

(c)

EXAMPLE 1

To a solution of 2-acetoxymethyl-4-methanesulfonoxy-1-butyl acetate (b) (3.74 g, 83.0 wt %, 11 mmol) in DMF (35 ml) were added 2-amino-6-chloropurine (a) (1.70 g, 10 mmol) and potassium carbonate (2.07 g, 15 mmol), and the mixture was reacted at 30° C. for 22 hr and at 70° C. for 2 hr. The N-9-position alkylated form (c): N-7-position alkylated form (d) ratio at the time of completion of the reaction was 5.55:1 and the total amount of the reaction product was 3.5 g (calculation by HPLC). After the reaction, the reaction product was cooled to 20° C., acetic acid (1.2 ml, 21 mmol) and water (30 ml) were added, and pH was adjusted to 7.0. The mixture was heated to 50° C. to dissolve the crystal. This solution was made to gradually cool to 20° C. at 5° C./hr and stirred at 20° C. for 12 hr. Water (5 ml) was added and the mixture was stirred at 20° C. for 2 hr. The obtained crystal was filtrated, washed with 50 v/v % aqueous DMF solution (6 ml) and water (6 ml), and dried in vacuo at 50° C. overnight to give 2-acetoxymethyl-4-(2-amino-6-chloropurin-9-yl)-1-butyl acetate (c) (2.27 g, yield 63.8%) as a white crystal. The (c):(d) ratio of the obtained crystal was 1144:1.

$^1$H-NMR(CDCl$_3$): 7.81(s,1H,H-8), 5.18(brs,2H,NH$_2$), 4.21(t,2H,J=7.0 Hz,H-1'), 4.15(d,4H,J=5.4 Hz,H-4'), 2.07(s, 6H,2Ac), 2.03–1.90(m,3H,H-2',3')

EXAMPLE 2

To a solution of 2-acetoxymethyl-4-methanesulfonoxy-1-butyl acetate (b) (4.08 g, 83.0 wt %, 12 mmol) in 1,3-dimethyl-2-imidazolidinone (21 ml) were added 2-amino-6-chloropurine (a) (1.70 g, 10 mmol) and potassium carbonate (2.07 g, 15 mmol), and the mixture was reacted at 40° C. for 22 hr and at 70° C. for 2 hr. The N-9-position alkylated form (c):N-7-position alkylated form (d) ratio at the time of completion of the reaction was 5.13:1 and the total amount of the reaction product was 3.26 g (calculation by HPLC). After the reaction, the reaction product was cooled to 20° C., 1M aqueous hydrochloric acid solution (6 ml, 6 mmol) and water (15 ml) were added, and pH was adjusted to 7.0. The mixture was stirred at 20° C. for 4 hr. The obtained crystal was filtrated, washed with 50 v/v % aqueous 1,3-dimethyl-2-imidazolidinone solution (10 ml) and water (10 ml), and dried at 50° C. for 12 hr to give 2-acetoxymethyl-4-(2-amino-6-chloropurin-9-yl)-1-butyl acetate (c) (1.86 g, yield 52.3%) as a white crystal. The (c):(d) ratio of the obtained crystal was 189.5:1.

According to the present invention, a 2-amino-6-halopurine derivative (N-9-position alkylated form) represented by the aforementioned formula (3) can be selectively crystallized, whereby famciclovir known as an antiviral agent, and an intermediate compound therefor can be efficiently produced.

This application is based on patent application No. 2001-262301 filed in Japan, the contents of which are hereby incorporated by reference.

What is claimed is:

1. A method of producing a 2-amino-6-halopurine compound represented by formula (3), which comprises subjecting a mixture comprising 2-amino-6-halopurine compounds represented by formulae (3) and (5):

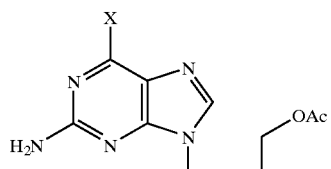

and

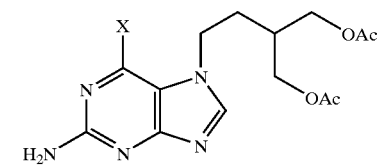

wherein X is a chlorine atom, a bromine atom or an iodine atom and Ac is an acetyl group, to a crystallization step using a mixed solvent of an organic solvent and water to selectively precipitate said 2-amino-6-halopurine compound represented by formula (3).

2. The method of claim 1, wherein said mixture comprising said 2-amino-6-halopurine compounds represented by formulae (3) and (5) is obtained by reacting a 2-amino-6-halopurine represented by the formula (1):

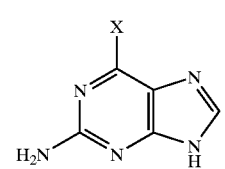

wherein X is as defined in claim 1, with a compound represented by formula (2):

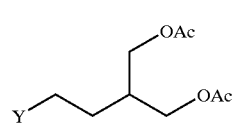

wherein Y is a leaving group and Ac is as defined in claim 1.

3. The method of claim 1 or 2, wherein X is a chlorine atom.

4. The method of claim 3, wherein said organic solvent is at least one selected from the group consisting of dimethylformamide, N-methylpyrrolidone, 1,3-dimethyl-2-imidazolidinone, dimethylacetamide, and mixtures thereof.

5. The method of claim 3, wherein said crystallization is cooling crystallization.

6. The method of claim 2, wherein said leaving group represented by Y is a group selected from the group consisting of a chlorine atom, a bromine atom, an iodine atom, a p-toluenesulfonyloxy group, a mesyloxy group, a trifluoromethanesulfonyloxy group, an alkylcarbonate group, a phenylcarbonate group and a saturated or unsaturated acyloxy group.

7. The method of claim 6, wherein said organic solvent is at least one selected from the group consisting of dimethylformamide, N-methylpyrrolidone, 1,3-dimethyl-2-imidazolidinone, dimethylacetamide, and mixtures thereof.

8. The method of claim 6, wherein said crystallization is cooling crystallization.

9. The method of claim 2, wherein said 2-amino-6-halopurine represented by formula (1) is reacted with said compound represented by formula (2) in the same organic solvent as used for crystallization.

10. The method of claim 9, wherein said organic solvent is at least one selected from the group consisting of dimethylformamide, N-methylpyrrolidone, 1,3-dimethyl-2-imidazolidinone, dimethylacetamide, and mixtures thereof.

11. The method of claim 9, wherein said crystallization is cooling crystallization.

12. The method of claim 2, wherein said 2-amino-6-halopurine represented by formula (1) is reacted with said compound represented by formula (2) in the presence of a base.

13. The method of claim 12, further comprising neutralization of a reaction mixture by using an acid after completion of the reaction.

14. The method of claim 13, wherein said crystallization is cooling crystallization.

15. The method of claim 12, wherein said crystallization is cooling crystallization.

16. The method of claim 2, wherein said organic solvent is at least one selected from the group consisting of dimethylformamide, N-methylpyrrolidone, 1,3-dimethyl-2-imidazolidinone, dimethylacetamide, and mixtures thereof.

17. The method of claim 2, wherein said crystallization is cooling crystallization.

18. The method of claim 1, wherein said organic solvent is at least one selected from the group consisting of dimethylformamide, N-methylpyrrolidone, 1,3-dimethyl-2-imidazolidinone, dimethylacetamide, and mixtures thereof.

19. The method of claim 18, wherein said crystallization is cooling crystallization.

20. The method of claim 1, wherein said crystallization is cooling crystallization.

21. A method of producing famciclovir represented by formula (4):

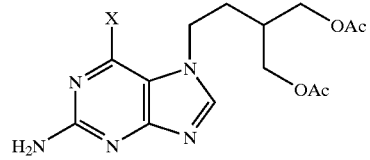

wherein Ac is an acetyl group, which comprises obtaining a 2-amino-6-halopurine compound represented by formula (3) by subjecting a mixture comprising 2-amino-6-halopurine compounds represented by formulae (3) and (5):

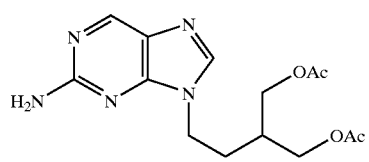

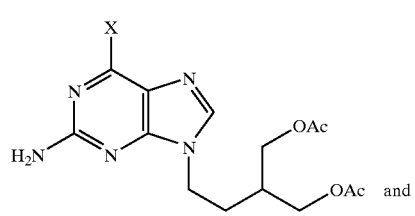

wherein X is a chlorine atom, a bromine atom or an iodine atom and Ac is an acetyl group, to a crystallization step by the method claim 1, and then reducing said 2-amino-6-halopurine compound represented by formula (3).

22. The method of claim 21, wherein said mixture comprising said 2-amino-6-halopurine compounds represented by formulae (3) and (5) is obtained by reacting a 2-amino-6-halopurine represented by formula (1):

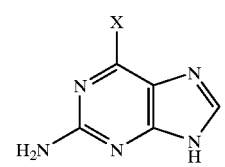

wherein X is as defined in claim 1, with a compound represented by formula (2):

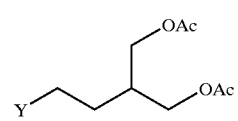

wherein Y is a leaving group and Ac is as defined in claim 1.

23. The method of claim 21 or 22, wherein X is a chlorine atom.

24. The method of claim 22, wherein said leaving group represented by Y is a group selected from the group consisting of a chlorine atom, a bromine atom, an iodine atom, a p-toluenesulfonyloxy group, a mesyloxy group, a trifluoromethanesulfonyloxy group, an alkylcarbonate group, a phenylcarbonate group and a saturated or unsaturated acyloxy group.

25. The method of claim 22, wherein said 2-amino-6-halopurine represented by formula (1) is reacted with said compound represented by formula (2) in the same organic solvent as used for crystallization.

26. The method of claim 22, wherein said 2-amino-6-halopurine represented by formula (1) is reacted with said compound represented by formula (2) in the presence of a base.

27. The method of claim 26, further comprising neutralization of a reaction mixture by using an acid after completion of the reaction.

28. The method of claim 21, wherein said organic solvent is at least one selected from the group consisting of dimethylformamide, N-methylpyrrolidone, 1,3-dimethyl-2-imidazolidinone, dimethylacetamide, and mixtures thereof.

29. The method of claim 21, wherein said crystallization is cooling crystallization.

30. A method of selectively crystallizing a 2-amino-6-halopurine compound represented by formula (3), which comprises subjecting a mixture comprising 2-amino-6-halopurine compounds represented by formulae (3) and (5):

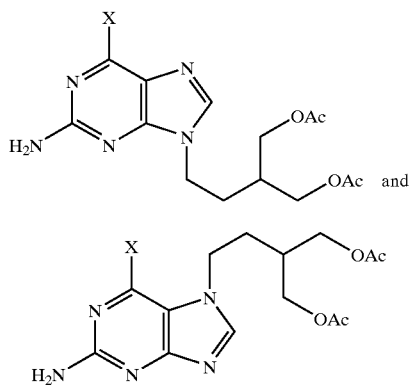

(3)

(5)

wherein X is a chlorine atom, a bromine atom or an iodine atom and Ac is an acetyl group, to a crystallization step using a mixed solvent of an organic solvent and water.

31. The method of claim 30, wherein X is a chlorine atom.

32. The method of claim 30, wherein said organic solvent is at least a member selected from the group consisting of dimethylformamide, N-methylpyrrolidone, 1,3-dimethyl-2-imidazolidinone, dimethylacetamide, and mixtures thereof.

33. The method of claim 30, wherein said crystallization is cooling crystallization.

* * * * *